United States Patent [19]

Erb

[11] Patent Number: 4,600,551
[45] Date of Patent: Jul. 15, 1986

[54] METHOD FOR PRODUCING BREAST PROSTHESES AND SUPPORTS

[76] Inventor: Robert A. Erb, Jug Hollow Rd., P.O. Box 86, Valley Forge, Pa. 19481

[21] Appl. No.: 612,618

[22] Filed: May 21, 1984

[51] Int. Cl.⁴ ............................................. B29C 41/12
[52] U.S. Cl. .......................... 264/222; 264/DIG. 30; 623/7
[58] Field of Search ...................... 264/222, DIG. 30; 623/7

[56] References Cited

U.S. PATENT DOCUMENTS 2,580,264 12/1951 Wright et al. ...................... 264/241
4,401,492 8/1983 Pfrommer ........................... 264/222

Primary Examiner—Donald Czaja
Assistant Examiner—V. Fischbach
Attorney, Agent, or Firm—Weiser & Stapler

[57] ABSTRACT

A method for producing an external breast prosthesis or support by forming a mold directly from the subject for whom the prosthesis is being prepared. After a molding material is applied to the subject's breast, the breast is immersed in an isodensity liquid to present the breast to a zero-gravity condition while the molding material cures.

25 Claims, 3 Drawing Figures

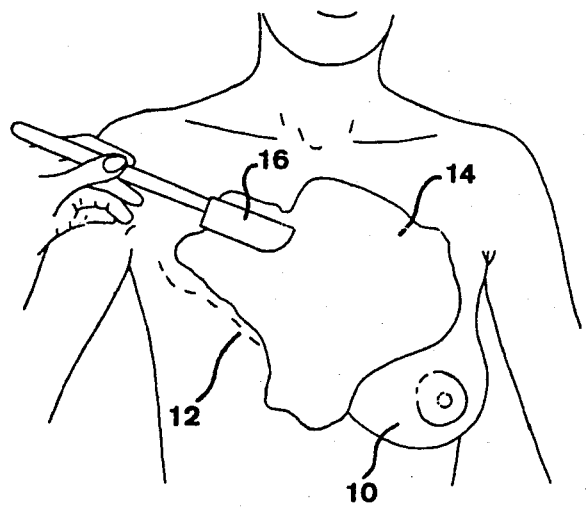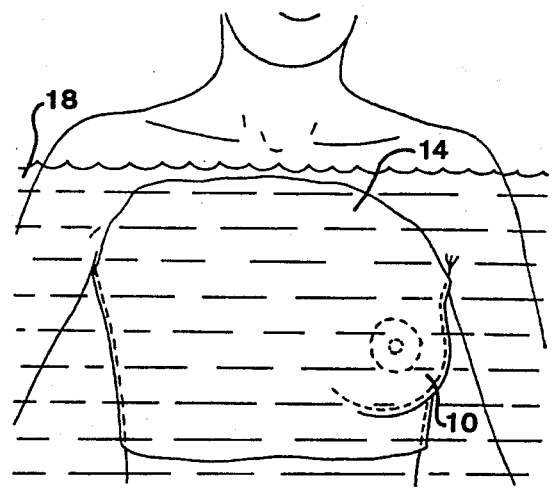
FIG. 1  FIG. 2
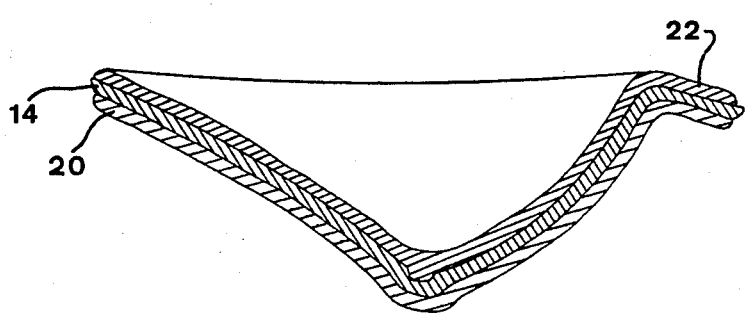
FIG. 3

METHOD FOR PRODUCING BREAST PROSTHESES AND SUPPORTS

DESCRIPTION

1. Technical Field

The present invention relates, in general, to the shaping of parts, and in particular, to a method for producing an external breast prosthesis or a breast support by developing a mold directly from the woman for whom the prosthesis or support is being prepared.

2. Background Art

The preferred practice for forming an external breast prosthesis is ideally to develop a mold from the breast of the woman for whom the prosthesis is being prepared and cast the prosthesis in the mold. The mold can be developed from the breast being replaced if the structure has not been deformed by disease. More commonly, however, the diseased breast is not a suitable master. Furthermore, the mastectomy has usually taken place before the maker of the external prostheses becomes involved.

In such case, the mold can be developed from the other breast, provided a mirror-image prosthesis is replicated from a cast fabricated in the primary mold. Co-filed application Ser. No. 612,613, now abandoned, in the name of Robert A. Erb and entitled "Reversing Pantograph", describes and claims an apparatus for producing such mirror-image replications of parts, including external body prostheses. The contents of this copending application are incorporated by reference in this application as if fully set forth herein.

Unfortunately, in making lifelike breast prostheses, it has not been possible to use a direct cast because of gravitational distortion of the breast from which the mold is formed, a problem which is further exacerbated by the additional initial distortion caused by the weight of the mold-making materials. This is because a soft replica made of the gravitationally-stressed structure still further distorts under its own gravitational stresses.

In the prior art (as shown, for example, by Charles Dame Clarke, "Prosthetics", The Standards Arts Press, Butler, MD, 1965, pp 155–178), in fabricating a custom-formed external breast prosthesis, a conventional mold (e.g., of an agar material with a gypsum plaster mother-mold) is made bilaterally of the mastectomy patient's chest. From this mold a cast (e.g., in gypsum plaster) is made. Over this cast an artist applies a breast shape in modeling material (e.g., wax) matching the remaining breast, but raised in shape and position compared with the remaining breast. The soft (optionally liquid filled) prosthesis cast from a mold of the formed breast shape would, following adhesive attachment to the chest wall, sag by elastic deformation under gravity to approximate the shape and position of the remaining breast. A disadvantage of this approach is that it does not provide a direct cast of an unstressed breast form and thus does not permit the use of a reversing pantograph in directly fabricating the master for the prosthesis. Instead, this prior art method requires the time-consuming efforts of a skilled artist, either in direct sculpture or in reshaping a wax cast derived from a donor. Further, it requires the artist to guess as to what would be the shape of the breast free from gravitational stresses.

Another approach in the prior art (Arthur O. Rahn and Louis J. Boucher, "Maxillofacial Prosthetics, Principles and Concepts", W.B. Saunders Company, Philadelphia, PA, 1970, pp 253–261) for custom-made breast prostheses involves supporting the remaining breast in half a brassiere, which is taped onto the chest wall, and making a conventional mold of the chest and a rigid cast from this mold. A breast form is then sculpted over the cast to match the brassiere-supported shape. A mold is made of the sculpted shape and the prosthesis is cast in this mold. One disadvantage of this method is that the breast is deformed into the shape of the brassiere and therefore the shape used as the master for the artist to follow does not represent the unstressed form of the remaining breast. An additional undesirable feature is that the outer texture of the rigid cast does not represent that of the breast itself, but instead that of the brassiere and attachment tapes. A drawback of this approach, also, is that it requires a skilled artist to sculpt the breast form.

While the present invention is primarily addressed in terms of the development of a breast prosthesis which may be prepared absent the deleterious effects of gravitation, it will be understood from the foregoing that similar considerations are presented in the manufacture of other breast supports, such as brassieres, since a brassiere which is correspondingly fitted to the breast will be capable of providing added support with improved comfort.

DISCLOSURE OF THE INVENTION

Accordingly, it is an object of the present invention to provide a new and improved method for producing an external breast prosthesis or support.

It is another object of the present invention to provide a method for producing a breast prosthesis or support from a mold formed from the breast of the woman for whom the prosthesis or support is being prepared.

It is another object of the present invention to provide a method for producing molds and casts which replicate precisely the contours of a breast structure as would exist in a condition where the breast is free from gravitational or other applied mechanical stresses.

It is a further object of the present invention to provide a method for producing a breast prosthesis or support which is free of distortions produced by the effect of gravity on the breast from which the mold is formed.

It is a further object of the present invention to provide a method for producing a brassiere of improved support and comfort.

It is a further object of the present invention to provide improved prostheses and supports produced in accordance with such methods.

These and other objects are achieved by forming a casting of a breast in a mold of the breast formed under a zero-gravity condition. By zero-gravity is meant a stress-free (zero gravitational stress) condition such as the human body would experience in the weightlessness of outer space. To this end, a molding material is applied to a breast to form a coating which upon hardening or curing will be a mold of the breast. Next, the coated breast is immersed in an isodensity (neutral-density) liquid to present the breast to a zero-gravity condition and to cure the molding material coating to form a mold of the breast under a zero-gravity condition. After the hardened mold is removed from the breast, a casting of the breast is formed in the hardened mold as a direct step toward forming a breast prosthesis, or the manufacture of a fitted brassiere.

BRIEF DESCRIPTION OF THE DRAWINGS

FIGS. 1 and 2 are partial views, in elevation, showing the production of a mold under zero-gravity conditions in accordance with the present invention.

FIG. 3 is a partial, sectional view of a mold and casting formed in accordance with the present invention.

BEST MODE OF CARRYING OUT THE INVENTION

FIGS. 1 and 2 show steps toward producing a breast prosthesis in accordance with the present invention for the case in which the subject has previously had a unilateral mastectomy. As shown in FIG. 1, the first step is to apply a molding material to the subject's breast 10, to the chest area 12 which represents the location for the future external prosthesis, and to adjacent areas. The molding material may be a liquid or a spreadable paste which cures to form a solid (e.g., and elastomer). A fast curing material such as Dow Corning SILASTIC 382 with stannous octoate catalyst may be used in this regard. If desired, a silicone rubber precursor molding material may be used with consistency modifiers such as pyrogenic silica to provide a yield value or an increase in consistency at low rates of shear (e.g., to reduce sag), or with consistency modifiers such as low viscosity polydimethylsiloxane fluid to reduce the viscosity at higher shear rates (e.g., to facilitate mixing). The molding material may be mixed in bowls or other vessels and may be applied with a flexible spatula 16 or other tool, or with the fingers. A non-air-entraining mixing and dispensing system may also be used in handling the molding material.

Next, the coated breast is immersed in an isodensity liquid to present the breast to a zero-gravity condition during which time the molding material coating cures to form a mold of the breast under a zero-gravity condition. This is shown in FIG. 2. As the coated breast 10 is immersed in the isodensity liquid 18, the breast structure is displaced upward, as is evident in comparing FIGS. 1 and 2. While the breast is in this position in isodensity liquid 18, coating 14 cures and a mold is formed. Various liquid solutions may be used as the isodensity liquid, depending upon the particular circumstances of forming the breast mold. For example, ordinary water is a suitable neutral-density liquid, with the density of the breast being slightly less than that of water and the density of a typical silicone rubber molding material being slightly more than that of water. In this way, the lower density breast and the higher density molding material balance out. If required, a lower density liquid can be obtained by the addition of ethyl alcohol or isopropyl alcohol to water and a higher density liquid can be obtained by addition of a salt, such as sodium chloride, or glycerol to water.

Ordinarily, the hardened breast mold will be relatively thin and easily deformable elastically. In order to maintain the shape of the mold during subsequent casting operations, a rigid mother-mold or outer shell may be applied over the outside surface of the hardened breast mold to build it up. This may be done while the breast mold is still immersed in the isodensity liquid using, for example, a water-curing polymer bandage material. It may also be done subsequent to removal of the subject with the breast mold in place from the isodensity liquid using, for example, a plaster bandage material. Significant distortion does not occur in this case with a silicone rubber mold because the cured mold material is much stiffer than the soft tissue of the breast and confines the breast closely to the zero-gravity shape. A third method for making a mother-mold permits the mother-mold to be made after peeling the primary mold free from the subject's body. For this procedure a paste of a hardenable substance (e.g., a silica-filled epoxy composition) is spread on the outside (not on the skin side) of the elastomeric mold while the assembly is submerged in a liquid having a density the same as that of the assembly, with hardening of the mother-mold material being allowed to take place while the assembly is submerged.

Alternatives to making a mother-mold would include making the primary mold thick enough to be supportable without distortion in a bed of sand or the like, and lining the inside of the primary mold with the casting material (e.g., epoxy paste) and allowing this to harden while the combined system is immersed in neutral-density liquid.

As shown in FIG. 3, after the mold is formed from cured coating 14 and, removed from the subject, is supported by rigid mother-mold 20, it then is used to form a casting 22 which is a replica of breast 10 in its zero-gravity configuration and adjacent areas of the chest. In the less-common situation in which mold 14 is of the breast before being removed by mastectomy, cast 22 can either directly be the shell of the breast prosthesis, or through another molding step and casting step, can be used directly in the fabrication of the prosthesis.

For the more-common situation in which mold 14 has been made on a patient who has already undergone a unilateral mastectomy, a use of cast 22 is to provide a master shape from which a mirror-image replication of the breast form may be derived, for example, with the apparatus of the aforementioned copending application. For mirror-image replication, where a stylus may be used to follow the surface contours, cast 22 would preferably be made of a dimensionally stable, rigid material. Examples of suitable materials are dental stone or other gypsum plaster, low-melting alloy, epoxy resin, castable polyester resin, castable syntactic foam, and rigid polyurethane foam. The portion of cast 22 which replicates the half of the chest where the mastectomy has been performed can serve directly as the back part of the mold for fabricating the prosthesis.

A special, thin-wall cast 22 may be used as an overlay for providing realistic skin texture on a mirror-image breast form as would be carved with a reversing pantograph. Materials suitable for this application include beeswax and low-molecular-weight polyethylenes. The skin-texture overlays may be softened by heating their reverse side to conform to the contours of the carved mirror-image breast. Areas between adjacent overlays can be filled with a modeling clay which can be smoothed and then texturized with skin-molded texturizing tools (e.g., molded in epoxy resin). A mold is made of the skin-textured, mirror-image model. This mold can be made from epoxy resin reinforced with fiberglass (e.g., by casting and hand lay-up) or filled with aluminum powder. From this final mold the prosthesis is fabricated. The prosthesis, which may be formed in layers with intrinsic coloration, may consist of an elastomeric outer skin with gel and/or liquid filling material.

Another application of the zero-gravity procedure of molding the breast in its stress-free configuration is in the fabrication of custom formed brassieres. The mold 14 or a cast 22 from the mold may be used to fabricate the brassiere cups directly; for example, by piecing a paper pattern or fabric in the mold or on the cast, or by thermoforming a fabric made of a thermoplastic material in the mold or over the cast. The described zero-gravity molding procedure allows for the first time direct replicative fabrication of a brassiere configuration which can provide stress-free support of the breast structure.

While in the foregoing there has been described a preferred embodiment of the present invention, it should be understood to those skilled in the art that various modifications and changes can be made without departing from the true spirit and scope of the invention as recited in the claims.

What is claimed is:

1. A method for replicating a breast comprising the steps of:
   applying a molding material to the breast to form a coating which upon hardening will be a mold of the breast;
   immersing the coated breast in a liquid having essentially the same density as that of the coated breast to present the breast to an essentially zero-gravity condition while said molding material coating cures to form a hardened mold of the breast under a zero-gravity condition;
   removing the hardened mold from the breast; and
   forming a casting of the breast in said hardened mold.

2. A method according to claim 1 wherein said molding material is a fast curing silicone elastomer system.

3. A method according to claim 2 further including the step of modifying the consistency of said elastomer system.

4. A method according to claim 3 wherein said consistency modifier is added to said elastomer system to provide a yield value.

5. A method according to claim 3 wherein said consistency modifier is added to said elastomer system to reduce viscosity.

6. A method according to claim 2 wherein said liquid is water.

7. A method according to claim 6 further including the step of adjusting the density of said liquid.

8. A method according to claim 1 further including the step of rigidifying said breast mold by applying a molding material to the outside surface of said breast mold.

9. A method according to claim 8 wherein said breast mold is rigidified by applying a water-activated curing material to the breast mold while it is immersed in said liquid.

10. A method according to claim 8 wherein said breast mold is rigidified by applying a plaster material to the breast mold after it has been removed from said liquid.

11. A method according to claim 8 wherein said breast mold is rigidified by applying a paste of a hardenable substance to the outside of said breast mold while submerged in a liquid having essentially the same density as that of the breast mold and paste assembly, and allowing said paste to harden while submerged in said liquid.

12. A method according to claim 1 further including the steps of:
   supporting said breast mold in a bed of sand;
   lining the inside of said breast mold with a a casting material; and
   immersing said supported, lined breast mold in the liquid while said casting material hardens.

13. A method according to claim 1 wherein the casting of the breast forms a breast prosthesis.

14. A method according to claim 1 wherein the casting of the breast is a master shape for use in forming a breast prosthesis.

15. A method according to claim 14 further including the step of forming a mirror-image replication of said casting.

16. A method according to claim 15 wherein said mirror-image replicat.oni is formed using reversing pantograph.

17. A method according to claim 16 wherein said casting is formed of a dimensionally stable material.

18. A method according to claim 1 further including the step of forming a thin-walled casting of the breast in said hardened mold for use as an overlay in combination with said casting.

19. A method according to claim 1 wherein the casting of the breast forms a cup of a brassiere.

20. A method according to claim 1 wherein the casting of the breast is used in forming a cup of a brassiere.

21. A method for replicating a breast and chest portions adjacent to said breast, comprising the steps of:
   applying a molding material to the breast and the adjacent chest portions to form a coating which upon hardening will be a mold of the breast and the adjacent chest portions;
   immersing the coated breast and the adjacent chest portions in a liquid having essentially the same density as that of the coated breast to present the breast and the adjacent chest portions to an essentially zero-gravity condition while said molding material coating cures to form a hardened mold of the breast and the adjacent chest portions under a zero-gravity condition;
   removing the hardened mold from the breast and the adjacent chest portions; and
   forming a casting of the breast and the adjacent chest portions in said hardened mold.

22. A method according to claim 18 wherein breast portions of said casting are used in forming a breast prosthesis, and chest portions of said casting are used in forming a backing for said breast prosthesis.

23. A prosthesis comprising a stress-free casting produced in accordance with the method of claim 1.

24. A prosthesis comprising a shaped member formed from a stress-free casting produced in accordance with the method of claim 1.

25. A brassiere comprising a cup fabricated from a stress-free casting produced in accordance with the method of claim 1.

* * * * *